(12) United States Patent
Lavigna et al.

(10) Patent No.: US 7,749,223 B2
(45) Date of Patent: Jul. 6, 2010

(54) NAVIGATED FEMORAL AXIS FINDER

(75) Inventors: Nicholas Jon Lavigna, Upper Saddle River, NJ (US); Stuart L. Axelson, Jr., Succasunna, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 327 days.

(21) Appl. No.: 10/914,660

(22) Filed: Aug. 9, 2004

(65) Prior Publication Data
US 2006/0036149 A1  Feb. 16, 2006

(51) Int. Cl.
*A61B 17/56* (2006.01)
(52) U.S. Cl. ....................................................... 606/53
(58) Field of Classification Search .................. 606/62, 606/102, 53, 63, 65–68, 72, 73, 86–89, 95–99, 606/104; 600/424; 623/20.35, 20.36, 23.15, 623/23.21–23.23, 23.25, 23.35
See application file for complete search history.

(56) References Cited

U.S. PATENT DOCUMENTS

| | | | | |
|---|---|---|---|---|
| 4,423,721 A * | 1/1984 | Otte et al. | .................... | 606/100 |
| 4,917,111 A * | 4/1990 | Pennig et al. | .................. | 606/97 |
| 5,122,146 A * | 6/1992 | Chapman et al. | ............. | 606/102 |
| 5,611,345 A * | 3/1997 | Hibbeln | ....................... | 600/424 |
| 6,021,343 A | 2/2000 | Foley et al. | | |
| 6,126,659 A * | 10/2000 | Wack | ........................... | 606/60 |
| 6,226,548 B1 * | 5/2001 | Foley et al. | .................. | 600/426 |
| 6,385,475 B1 | 5/2002 | Cinquin et al. | | |
| 6,434,415 B1 | 8/2002 | Foley et al. | | |
| 6,468,279 B1 * | 10/2002 | Reo | .............................. | 606/79 |
| 6,951,562 B2 * | 10/2005 | Zwirnmann | ................... | 606/80 |
| 2002/0002330 A1 * | 1/2002 | Vilsmeier | ..................... | 600/407 |
| 2002/0065518 A1 * | 5/2002 | Naybour et al. | ................ | 606/86 |
| 2002/0193800 A1 * | 12/2002 | Kienzle et al. | ................. | 606/80 |
| 2002/0198448 A1 * | 12/2002 | Zuk et al. | ...................... | 600/414 |
| 2003/0109883 A1 * | 6/2003 | Matsuzaki et al. | ............. | 606/86 |
| 2003/0171756 A1 * | 9/2003 | Fallin et al. | .................... | 606/80 |
| 2003/0196671 A1 * | 10/2003 | Sasso | ........................... | 128/899 |
| 2004/0152955 A1 * | 8/2004 | McGinley et al. | ............ | 600/300 |
| 2005/0065533 A1 * | 3/2005 | Magen et al. | ................ | 606/102 |

* cited by examiner

*Primary Examiner*—Eduardo C Robert
*Assistant Examiner*—David Comstock
(74) *Attorney, Agent, or Firm*—Lerner, David, Littenberg, Krumholz & Mentlik, LLP

(57) ABSTRACT

A long bone axis finder has a shaft extending along an axis and a first and second end. A tip portion is provided for releasable coupling to the shaft first end. A wedge element having an open side is provided for lateral engagement with said shaft. The wedge element is slidable along said shaft in a direction from the second to the first end. The axis finder is inserted into a long bone medullary canal until the tip portion engages a narrower portion of the canal. The wedge portion which is larger than the tip is laterally placed on the shaft and engages a portion of the canal closer to the shaft second end.

16 Claims, 5 Drawing Sheets

NAVIGATED FEMORAL AXIS FINDER

BACKGROUND OF THE INVENTION

This invention relates to navigated instrumentation for the preparation of the proximal femur for receiving a prosthetic femoral component. More particularly, the invention relates to a femoral axis finder which can be used with an optical computer-aided navigation system to accurately locate the femoral axis utilizing a shaft with a proximal and distal wedge for insertion in the medullary canal of the femur.

Navigation systems are an interactive operative monitoring system designed to improve the surgical performance and clinical outcome of Total Hip Arthroplasty. A computer-aided, image-less guidance system provides accurate decision making for alignment and orientation of instruments, trials and ultimately implants. The system may provide surgeons pre-operative, intra-operative and post-operative assessments of the patient's joint kinematic measurements. Use of a computer-aided surgical navigation system results in decreased morbidity and shorter hospitalization. Such systems are described in U.S. Pat. Nos. 6,021,343, 6,385,475 and 6,434,415, the teachings of which are incorporated herein by reference.

In the past, the medullary canal of the femur has been opened by standard operative techniques. The surgeon would then digitize the distal and proximal points on a canal axis finder, which finder may be a shaft with a T-handle and a proximal plug for engaging the proximal femur. The shaft is digitized by touching two points on the shaft with a pointer optically coupled to the computer navigation system. Normally, the pointer would have multiple light emitting diodes which, upon activation, emit light which can be read by one or more cameras in the operating room which are connected to the computer-aided navigation system. Digitizing the distal and proximal points on the axis finder allows the navigation system to determine the axis along which a femoral broach has to be aligned to prepare the femoral canal. For patients with varus/valgus deformity, the shaft axis may deviate significantly from the anatomical axis of the femur. This deviation can be calculated by the navigation system and displayed on a CRT showing the proximal femur and the shaft axis.

Specifically, the shaft axis is digitized by inserting the optical tracker tip through the axis finder handle and digitizing a first distal point thereon and then inserting the tracker's tip through the handle to digitize a second point thereon located proximally of the first point on the axis finder. The navigation system checks the distance between the digitized distal and proximal points. Once the shaft axis has been digitized, the surgeon can proceed with preparing the femur. The surgeon removes the axis finder and can then insert a broach into the canal, which broach includes an optical tracker preferably on the broach handle. Thus, the navigation system can align the axis of the broach and the proper anteversion/retroversion angle in the proper frontal offset and varus/valgus angle of the broach. The axes of the broach is shown on the CRT display along with the axis found by the axis finder so that the surgeon can align the axes.

One drawback of this system is that it is difficult to get a snug fit both proximally and distally for all size femurs while using a single shaft axis finder. Thus, the present invention provides for a modular system having a plurality of distal and proximal spacers.

SUMMARY OF THE INVENTION

One aspect of the invention is to accurately locate the femoral axis and have the ability to translate that axis to a computer-aided navigation instrument device.

In the present invention, a "wedge" device is used to locate two spaced points within the canal that best represent a circular cross-section. These two points then represent the location and trajectory of the proximal femoral axis. The navigation "smart" instrument may be used in one of two ways. The first would be to use a navigation pointer to digitize the shaft of the instrument. The second would be to use one of the optical trackers mounted to a post on the instrument itself.

The axis finder instrument assembles and functions in the following manner. The first step is optional and reflects a method of removing the instrument and/or placing the femoral sleeve wedges into the canal. One first assembles an insertion sleeve over the instrument shaft until it butts up against the distal surface of the instrument handle at the shaft proximal end. The second step is to assemble the appropriate distal-sizer onto the distal end of the instrument shaft.

The third step is to plunge the distal end of the instrument into the proximal femoral canal until the distal sizer "wedges" and stops. This wedging occurs because the femoral canal gradually narrows on moving towards the isthmus of the canal. The fourth step is to assemble one of the proximal sizer wedge devices onto the shaft by side loading it onto the shaft. The proximal sizer wedge devices preferably come in at least four (4) different sizes, for example, ranging from 10-15 mm, 15-20 mm, 20-25 mm, and 25-30 mm.

The fifth step is to drive the proximal wedge device into the femoral canal. Optimally one would wedge the device at a level of about 20 mm below the midpoint of the lesser trochanter. This may be achieved by using the insertion sleeve which screws into the end of the proximal wedge device or by pushing the device into the canal with the fingers or forceps. Once both the distal sizer and the proximal wedge are located, a navigation instrument may be used to digitize the central axis. This may be done by putting the navigation pointer down the handle of the instrument in line with the femoral axis and digitizing at least two points. It may also be accomplished by using an optical navigation tracker that is mounted on the axis finder a fixed distance and angle from the instrument shaft. The digitized axis is then transmitted to the navigation unit through the navigation trackers and camera technology.

By accurately locating the axis of the femoral canal over a distance of 50-100 mm and being able to transfer that information to a navigation system, it allows the surgeon to know the precise location of the femoral canal during preparation and final implant insertion. Therefore, by using navigation in the preparation and final prosthesis insertion process, the surgeon can understand the relationship between the femoral axis and either the broach or the final prosthesis. Thus, the surgeon can judge varus/valgus angle of the broach and/or stem.

DETAILED DESCRIPTION

Figure 1:
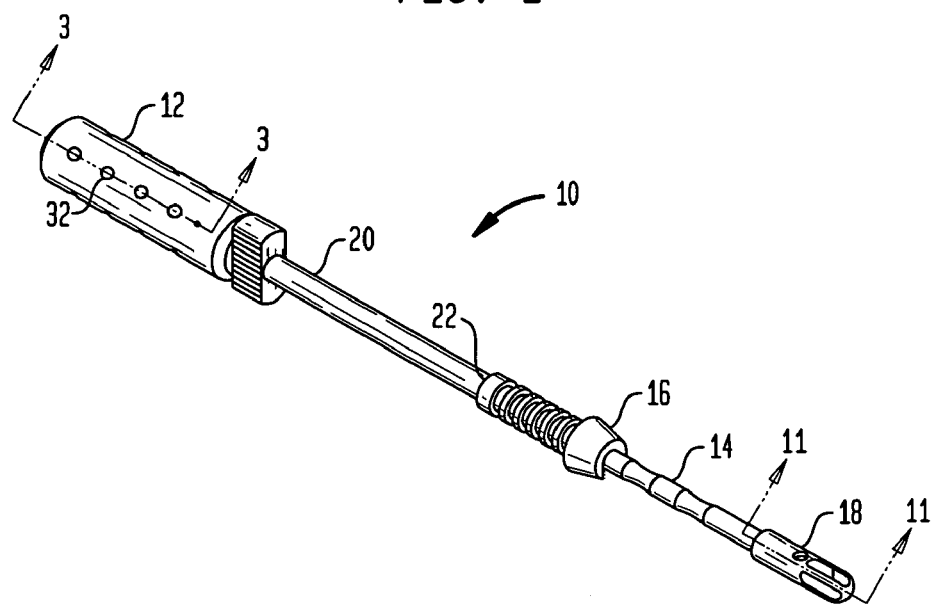
FIG. 1 is a perspective view of the navigated femoral axis finder of the present invention.
Figure 2:
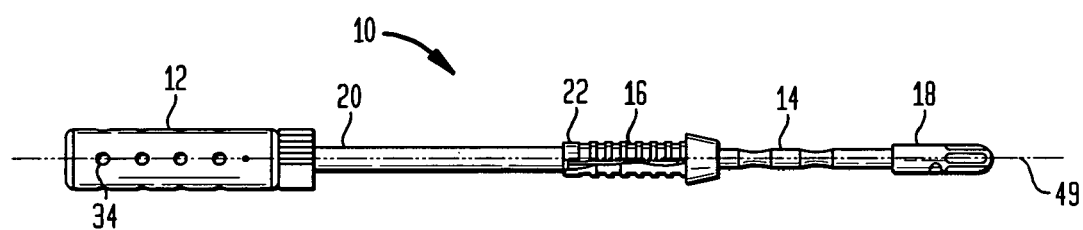
FIG. 2 is a side view of the femoral axis finder of FIG. 1.

Referring to FIGS. 1 and 2, there is shown the navigated femoral axis finder instrument of the present invention generally denoted as 10. While the axis finder of the present invention is described for use with a femur it could just as easily be used with other long bones such as the tibia and humerus. The axis finder 10 has a proximal handle portion 12, a shaft 14, a proximal wedge 16 and a generally cylindrical distal extension or tip 18. An insertion, sleeve 20 is provided on shaft 14 for sliding engagement therewith. Insertion sleeve 20 slides on shaft 14 and contacts the proximal end 22 of the proximal sizer 16 to move the sizer into contact the bone in the proximal medullary canal after insertion of the femoral axis finder therein. Of course, the surgeon could use other means of moving proximal wedge 16 into a tight fit with the canal.

Figure 3:
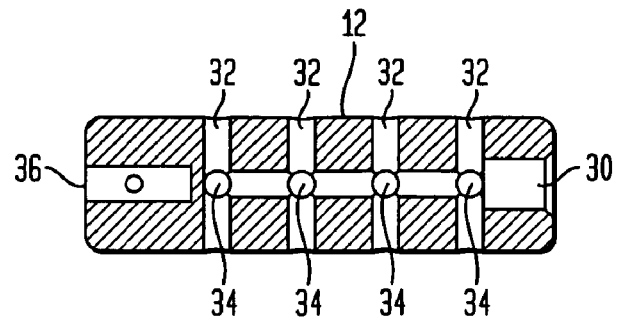
FIG. 3 is an enlarged cross-sectional view of the femoral axis finder handle of FIG. 1 along lines 3-3.

Referring to FIG. 3, there is shown a cross-sectional view of handle 12 along lines 3-3. Handle 12 has a receptacle 30 at a distal end thereof for receiving the proximal end of shaft 14. Handle 12 also includes a plurality of cross-bores 32 and 34 which are provided for receiving a tip an optical navigation system tracker as will be discussed in more detail below. In addition, handle 12 includes an axial aligned bore 36 which is co-axial with socket 30 and therefore co-axial with shaft 14 after assembly. In the preferred embodiment, handle 12 is made of a stainless steel material such as 17-4 stainless steel.

Figure 4:
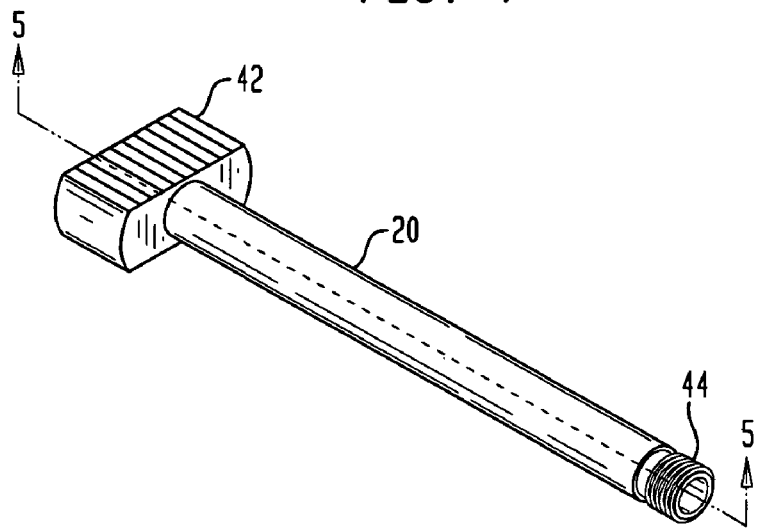
FIG. 4 is a perspective view of the insertion sleeve of the femoral axis finder of FIG. 1.
Figure 5:
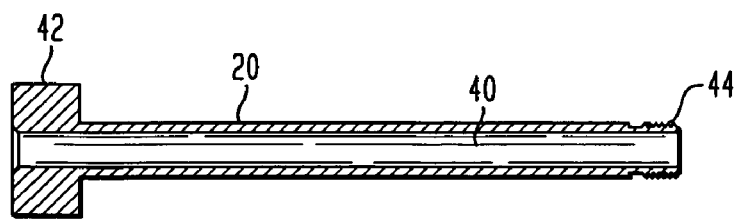
FIG. 5 is a cross-sectional view of the insertion sleeve of FIG. 4 along lines 5-5.

Referring to FIGS. 4 and 5, there is shown insertion sleeve 20 prior to its being mounted on shaft 14. Insertion sleeve 20 has a hollow bore 40 adapted to slidingly engage the outer diameter of shaft 14. At the proximal end of sleeve 20 is a gripping element 42 which can be grasped between the thumb and forefinger to slide sleeve 20 along shaft 14 in the distal direction. In the preferred embodiment, sleeve 20 includes a threaded end 44 which is adapted to threadably engage the proximal end of proximal wedge 16. The threading is optional and the end 44 can be made non-threaded and still act to push wedge 16 in the distal direction.

Figure 6:
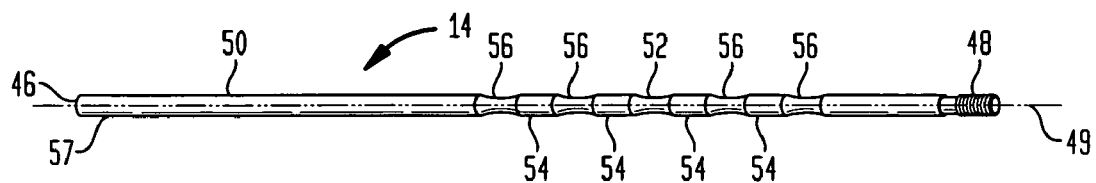
FIG. 6 is a perspective view of the shaft of the femoral axis finder of FIG. 1.

Referring to FIG. 6, there is shown shaft 14 which includes a proximal end 46 and a preferably threaded distal end 48. In the preferred embodiment, shaft 14 extends along axis 49 and has a first generally cylindrical section 50 and a second undulating section 52. Undulating section 52 includes cylindrical portions 54 separated by concave portions 56. Proximal end 46 may include a cross-bore 57 to enable shaft 14 to be pinned to handle 12.

Figure 7:
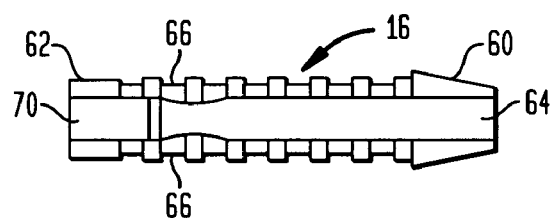
FIG. 7 is a side view of the proximal wedge of the navigated femoral axis finder of FIG. 1.
Figure 8:
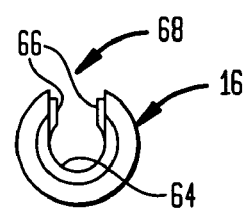
FIG. 8 is an end view of the proximal wedge of FIG. 7.

Referring to FIGS. 7 and 8, there is shown an enlarged view of proximal wedge 16 which, in the preferred embodiment, includes a first conically tapered end 60, a proximal end 62 and a throughbore 64. Throughbore 64 is preferably threaded at end 62 and includes a pair of convex surfaces 66 extending into bore 64 adjacent threaded end 62. As best seen in FIG. 8, wedge 16 is open along one side 68 so that it may be inserted onto shaft 14 in a direction transverse to the axis 49 of shaft 14. Once placed on shaft 14, concave inwardly extending surfaces 66 engage any one of the concave surface segments 56 to allow wedge 16 to be held onto shaft 14 both laterally and in its longitudinal position along axis 49 in a plurality of different axial positions. Preferably, wedge 16 is made of a polymeric material and has sufficient flexibility to allow surfaces 66 to expand on contacting cylindrical surface 54 and to snap inwardly and hold on portions 56 of shaft 14. Thus, portions 56 act as discrete stops along the shaft. In the preferred embodiment, wedge 16 includes threaded proximal bore 70 can engage the threaded section 44 of sleeve 20.

Figure 9:
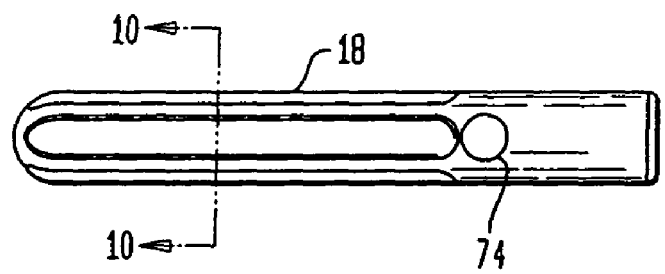
FIG. 9 is a side view of the cylindrical distal section of the femoral axis finder of FIG. 1.
Figure 10:
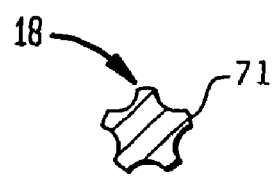
FIG. 10 is a cross-sectional view of the cylindrical distal extension of FIG. 9 along lines 10-10.
Figure 11:
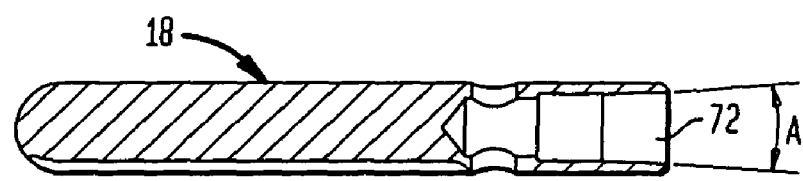
FIG. 11 is a cross-sectional view of the cylindrical distal extension along lines 11-11 of FIG. 1.

Referring to FIGS. 9 through 11, there is shown the distal extension 18 of the present invention which may also be made of a stainless steel material. In the preferred embodiment, extension 18 has a generally cylindrical shape and includes five protrusions 71 symmetrically oriented about the outer circumference. The use of the protrusions avoids pressure building in the canal during insertion of the instrument. As best seen in FIG. 11, the proximal end of the distal extension 18 includes a bore 72 which, in the preferred embodiment, has a taper "A" to allow for the ease of insertion of the distal tip of shaft 14. In the preferred embodiment, extension 18 includes a transverse bore 74.

Figure 12:
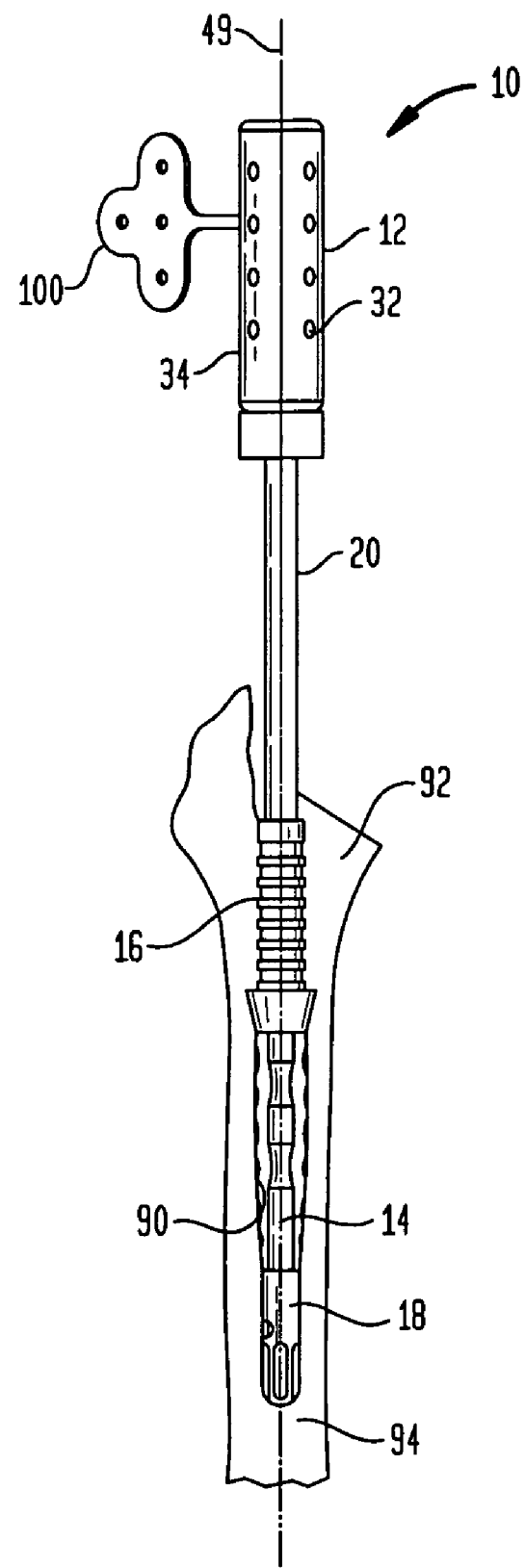
FIG. 12 is a view of the axis finder being used within a femur.

Referring to FIG. 12, there is shown the femoral axis finder 10 of the present invention inserted into the medullary canal 90 of a femur 92.

Referring to FIG. 12, the preferred method of use of the navigated femoral axis finder involves sliding insertion sleeve 20 onto the proximal end of shaft 14 and attaching the distal extension 18 to the distal end of shaft 14. Preferably, the handle 12 is fixedly attached to the proximal end of shaft 14 prior to use of the insertion sleeve. The proximal wedge 16 may then be inserted laterally onto the shaft 14. The distal end of the assembly is then placed in the medullary canal of the femur and moved towards the isthmus 94 of the canal until the distal extension engages the isthmus 94. To ensure engagement, a kit of distal extensions increasing in 1 mm increments from, in the preferred embodiment, 11 mm to 20 mm are provided to accommodate various size femurs. Once the distal extension is engaged in the isthmus, the surgeon moves the proximal wedge distally by grasping holding part 42 of insertion sleeve 20 moving the proximal wedge distally. This is done until the enlarged distal end 60 of proximal wedge 16 engages bone. To accommodate various size femurs, a kit of parts wherein the proximal wedge maximum diameter varies in 1 mm or 2 mm increments from between 10 mm and 30 mm is provided. If, intraoperatively, the surgeon is not able to seat the proximal wedge in a proper position within the femur, he can easily remove one size femoral wedge by moving it laterally off the shaft and substituting a larger size femoral wedge, again mounting it by moving it in a direction transverse to the shaft. The interaction of convex portion 66 and concave shaft portion 56 allows the surgeon to move the wedge distally and fix it on shaft 14 in an axial position where it contacts bone in the proximal femur. In addition, if necessary, the kit may include various lengths of shaft 14 to accommodate different size femurs.

Once the proximal wedge engages bone in the proximal femur, shaft 14 is closely aligned with the axis of the femur and then the handle portion 12 can be used to digitize the location of the axis 49. In one embodiment, this is done by taking the standard tracker 100 shown in FIG. 12 and inserting it either into the axial handle hole 36 or into one of the cross-bore holes 32 and 34 (as shown) which extend perpendicularly to the axis 49. Once the tracker pointer has been properly positioned in handle 12, its location is digitized and the axis calculated by the optical tracking system and computer system in the operating room and then stored in the computer. The axis orientation can be later used in aligning the femoral rasp broach or reamer to prepare the canal and also to align the femoral component for proper insertion and orientation within the canal. Once the navigation system tracks and stores the axis 49, the navigated femoral axis finder can be removed.

Alternately, the optical tracker can be releasably mounted on the tracker handle 12 or on the proximal end of shaft 14.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A kit of instruments determining an axis of a femur based on a femur intramedullary canal comprising:
an axially extending shaft having a proximal and a distal end, the proximal end having a location element for positioning a pointer of an optical navigation system thereon;
a plurality of distal sizers of different sizes for releasably engaging the distal end of said shaft the distal sizers having a central longitudinal axis co-axial with a longitudinal axis of the shaft when engaging the shaft;
a plurality of proximal sizers of differing sizes each having a proximal and a distal end for releasably engaging said proximal shaft end and slidably moveable axially therealong after said releasable engagement in the proximal to distal direction, each proximal sizer having a u-shaped recess with an open side extending axially from the proximal to the distal end thereof allowing for the releasable engagement with said shaft by movement in a direction transverse to a longitudinal axis of said shaft, the proximal sizers having a central longitudinal axis co-axial with both the shaft longitudinal axis and the distal sizer longitudinal axis when engaged on the shaft the proximal sizers independent of the distal sizers; wherein the proximal sizers are wedge elements having a conical surface formed adjacent a distal end thereof and formed about the central longitudinal axis of the proximal sizer and the U-shaped recess having a bore with an open side for engagement with a shaft by movement of said wedge element in a direction transverse to a shaft longitudinal axis and slidable axially along said shaft after being mounted thereon in a direction from said proximal to said distal end, the bore in the U-shaped recess including a radially inwardly extending stop element for engaging the shaft; and
an insertion sleeve engageable with the proximal shaft end for moving said proximal sizer from the proximal end towards the distal end of the shaft.

2. The kit as set forth in claim 1 wherein said insertion sleeve has a threaded end and said proximal sizer has a mating threaded end for coupling said sleeve to said sizer.

3. The kit as set forth in claim 1 wherein said proximal end of said shaft includes a handle portion.

4. The kit as set forth in claim 1 wherein said distal shaft end includes a threaded tip and each of said distal sizers include a threaded bore for engaging said threaded shaft tip.

5. The kit as set forth in claim 1 wherein said shaft includes a series of stops positioned at different positions along said longitudinal axis of the shaft for engaging the bore stop element for locating said wedge elements on the shaft.

6. The kit as set forth in claim 1 wherein said shaft proximal end includes a handle.

7. The kit as set forth in claim 6 wherein said handle includes at least one bore either parallel to or perpendicular to said shaft axis.

8. The kit as set forth in claim 1 further comprising an insertion sleeve slidably mounted on said shaft for engaging an end of said proximal sizer.

9. The kit as set forth in claim 1 wherein said wedge conical surface extends from said open side of said wedge around an outer surface of said shaft.

10. A kit of instruments determining an axis of a femur based on a femur intramedullary canal comprising:
an axially extending shaft having a proximal and a distal end, the proximal end having a location element for positioning a pointer of an optical navigation system thereon;
a plurality of distal sizers of different sizes for releasably engaging the distal end of said shaft the distal sizers having a central longitudinal axis co-axial with a longitudinal axis of the shaft when engaging the shaft; and
a plurality of proximal sizers of differing sizes each having a proximal and a distal end for releasably engaging said proximal shaft end and slidably moveable axially therealong after said releasable engagement in the proximal to distal direction, each proximal sizer having a u-shaped recess with an open side extending axially from the proximal to the distal end thereof allowing for the releasable engagement with said shaft by movement in a direction transverse to a longitudinal axis of said shaft, the proximal sizers independent of the distal sizers wherein said insertion sleeve has a threaded end and said proximal sizer has a mating threaded end for coupling said sleeve to said sizer the proximal sizers having a central longitudinal axis co-axial with both the shaft longitudinal axis and the distal sizer longitudinal axis when engaged on the shaft wherein the proximal sizers are wedge elements having a conical surface formed adjacent distal end thereof and formed about the central longitudinal axis of the proximal sizer and having a bore with an open side for engagement with a shaft by movement of said wedge element in a direction transverse to a shaft longitudinal axis and slidable axially along said shaft after being mounted thereon in a direction from said proximal to said distal end, the U-shaped recess including a radially inwardly extending stop element for engaging the shaft.

11. A kit of instruments determining an axis of a femur based on a femur intramedullary canal comprising:
an axially extending shaft having a proximal and a distal end, the proximal end having a location element for positioning a pointer of an optical navigation system thereon;
a plurality of distal sizers of different sizes for releasably engaging the distal end of said shaft the distal sizers having a central longitudinal axis co-axial with a longitudinal axis of the shaft when engaging the shaft; and
a plurality of proximal sizers of differing sizes each having a proximal and a distal end for releasably engaging said proximal shaft end and slidably moveable axially therealong after said releasable engagement in the proximal to distal direction, each proximal sizer having a u-shaped recess with an open side extending axially from the proximal to the distal end thereof allowing for the releasable engagement with said shaft by movement in a direction transverse to a longitudinal axis of said shaft, the proximal sizers independent of the distal sizers wherein the proximal sizers are wedge elements having a conical surface formed adjacent a distal end thereof and having an open side for engagement with a shaft by movement of said wedge element in a direction transverse to a shaft longitudinal axis and slidable axially along said shaft after being mounted thereon in a direction from said proximal to said distal end the proximal sizers having a central longitudinal axis co-axial with both the shaft longitudinal axis and the distal sizer longitudinal axis when engaged on the shaft wherein the proximal sizers are wedge elements having a conical surface formed adjacent a distal thereof and formed about the central longitudinal axis of the proximal sizer and the U-shaped recess having a bore with an open side for engagement with a shaft by movement of said wedge element in a direction transverse to a shaft longitudinal axis and slidable axially along said shaft after being mounted thereon in a direction from said proximal to said distal end, the bore in the U-shaped recess including a radially inwardly extending stop element for engaging the shaft.

12. The kit as set forth in claim 11 wherein said shaft includes a series of stops positioned at different positions along said longitudinal axis of the shaft for locating said wedge elements.

13. The kit as set forth in claim 12 wherein said shaft proximal end includes a handle.

14. The kit as set forth in claim 13 wherein said handle includes at least one bore either parallel to or perpendicular to said shaft axis.

15. The kit as set forth in claim 11 wherein said wedge conical surface extends from said open side of said wedge around an outer surface of said shaft.

16. A kit of instruments determining an axis of a femur based on a femur intramedullary canal comprising:

an axially extending shaft having a proximal and a distal end, the proximal end having a location element for positioning a pointer of an optical navigation system thereon;

a plurality of distal sizers of different sizes for releasably engaging the distal end of said shaft the distal sizers having a central longitudinal axis co-axial with a longitudinal axis of the shaft when engaging the shaft;

a plurality of proximal sizers of differing sizes each having a proximal and a distal end for releasably engaging said proximal shaft end and slidably moveable axially therealong after said releasable engagement in the proximal to distal direction, each proximal sizer having a u-shaped recess with an open side extending axially from the proximal to the distal end thereof allowing for the releasable engagement with said shaft by movement in a direction transverse to a longitudinal axis of said shaft, the proximal sizers independent of the distal sizers further comprising an insertion sleeve slidably mounted on said shaft for engaging an end of said proximal sizer the proximal sizers having a central longitudinal axis co-axial with both the shaft longitudinal axis and the distal sizer longitudinal axis when engaged on the shaft wherein the proximal size are wedge elements having a conical surface formed adjacent a distal end thereof and formed about the central longitudinal axis of the proximal sizer and the U-shaped recess having a bore with an open side for engagement with a shaft by movement of said wedge element in a direction transverse to a shaft longitudinal axis and slidable axially along said shaft after being mounted thereon in a direction from said proximal to said distal end, the bore in the U-shaped recess including a radially inwardly extending stop element for engaging the shaft.

* * * * *

UNITED STATES PATENT AND TRADEMARK OFFICE
CERTIFICATE OF CORRECTION

PATENT NO. : 7,749,223 B2  
APPLICATION NO. : 10/914660  
DATED : July 6, 2010  
INVENTOR(S) : Nicholas Jon LaVigna et al.

Page 1 of 2

It is certified that error appears in the above-identified patent and that said Letters Patent is hereby corrected as shown below:

Title page, [57] Abstract, line 2, "and a first and second end." should read --and first and second ends.--.
Column 1, line 11, "with a proximal and distal wedge" should read --with proximal and distal wedges--.
Column 1, line 14, "are an interactive" should read --are interactive--.
Column 1, line 15, "system" should read --systems--.
Column 1, line 62, "the broach is" should read --the broach are--.
Column 2, line 59, "judge varus/valgus" should read --judge the varus/valgus--.
Column 3, line 30, "insertion, sleeve" should read --insertion sleeve--.
Column 3, line 41, "tip an optical" should read --tip of an optical--.
Column 4, line 17, "bore 70 can" should read --bore 70 which can--.
Column 5, line 33, "said shaft the distal" should read --said shaft, the distal--.
Column 5, line 41, "u-shaped" should read --U-shaped--.
Column 5, line 47, "axis when engaged" should read --axis, when engaged--.
Column 5, line 48, "sizers independent" should read --sizers are independent--.
Column 5, line 50, "a conical surface" should read --conical surfaces--.
Column 6, line 3, "include a threaded" should read --includes a threaded--.
Column 6, line 26, "said shaft the distal" should read --said shaft, the distal--.
Column 6, line 34, "u-shaped" should read --U-shaped--.
Column 6, line 38, "sizers independent" should read --sizers being independent--.
Column 6, line 41, "sizer the proximal" should read --sizer, the proximal--.
Column 6, line 46, "adjacent distal end" should read --adjacent a distal end--.
Column 6, line 62, "said shaft the distal" should read --said shaft, the distal--.
Column 7, line 3, "u-shaped" should read --U-shaped--.
Column 7, line 7, "sizers independent" should read --sizers being independent--.
Column 7, line 14, "distal end the proximal" should read --distal end, the proximal--.
Column 8, line 8, "said shaft the distal" should read --said shaft, the distal--.
Column 8, line 17, "u-shaped" should read --U-shaped--.

Signed and Sealed this  
Twentieth Day of December, 2011

David J. Kappos  
*Director of the United States Patent and Trademark Office*

CERTIFICATE OF CORRECTION (continued)
U.S. Pat. No. 7,749,223 B2

Column 8, line 21, "sizers independent" should read --sizers being independent--.
Column 8, line 23, "said proximal sizer" should read --said proximal sizer,--.
Column 8, line 27, "proximal size are" should read --proximal sizers are--.